(12) United States Patent
Morino et al.

(10) Patent No.: US 10,551,171 B2
(45) Date of Patent: Feb. 4, 2020

(54) OPTICAL MEASUREMENT DEVICE

(71) Applicant: OMRON Corporation, Kyoto-shi, Kyoto (JP)

(72) Inventors: Hisayasu Morino, Fukuchiyama (JP); Kenichi Matoba, Otsu (JP); Takahiro Suga, Fukuchiyama (JP)

(73) Assignee: OMRON Corporation, Kyoto (JP)

( * ) Notice: Subject to any disclaimer, the term of this patent is extended or adjusted under 35 U.S.C. 154(b) by 188 days.

(21) Appl. No.: 15/413,866

(22) Filed: Jan. 24, 2017

(65) Prior Publication Data
US 2017/0276475 A1 Sep. 28, 2017

(30) Foreign Application Priority Data

Mar. 24, 2016 (JP) .................................. 2016-060274

(51) Int. Cl.
*G01B 11/02* (2006.01)
*G01B 11/24* (2006.01)
(Continued)

(52) U.S. Cl.
CPC .......... *G01B 11/24* (2013.01); *G01B 11/0608* (2013.01); *G01B 11/14* (2013.01);
(Continued)

(58) Field of Classification Search
CPC ... G01B 9/020326; G01B 11/026; G01C 3/06
(Continued)

(56) References Cited

U.S. PATENT DOCUMENTS 6,674,572 B1   1/2004   Scheruble et al.
2010/0283989 A1  11/2010  Sesko
(Continued)

FOREIGN PATENT DOCUMENTS

CN   102506754 A   6/2012
CN   103673887 A   3/2014
(Continued)

OTHER PUBLICATIONS

Extended European Search Report dated Apr. 4, 2017 for European Application No. 17152140.4 in 9 pages.
(Continued)

*Primary Examiner* — Rebecca C Bryant
(74) *Attorney, Agent, or Firm* — Knobbe, Martens, Olson & Bear, LLP

(57) ABSTRACT

A white light confocal optical measurement device capable of detecting abnormalities in a received light waveform; the optical measurement device includes: a light source; an optical system; a light receiving unit; and a processor configured to compute the distance from the optical system to the measurement object on the basis of a received light intensity of the wavelength components received in the light receiving unit. The processor compares a received light intensity of a wavelength component to a reference value for the wavelength component for a plurality of wavelength components in a waveform representing the light received, and detects an abnormality in the received light waveform when the amount of change in the received light intensity compared to the reference value therefor is greater than or equal to a predetermined threshold for any wavelength component in the plurality of wavelength components.

16 Claims, 15 Drawing Sheets

(51) Int. Cl.
   *G01C 3/06* (2006.01)
   *G01B 11/14* (2006.01)
   *G01N 21/27* (2006.01)
   *G01B 11/06* (2006.01)

(52) U.S. Cl.
   CPC ............... *G01C 3/06* (2013.01); *G01N 21/27* (2013.01); *G01B 2210/50* (2013.01); *G01N 2201/068* (2013.01)

(58) Field of Classification Search
   USPC ........................................................ 356/609
   See application file for complete search history.

(56) References Cited

U.S. PATENT DOCUMENTS

| | | |
|---|---|---|
| 2010/0284025 A1 | 11/2010 | Sesko |
| 2013/0222815 A1 | 8/2013 | Patzwald |
| 2015/0009484 A1 | 1/2015 | Sesko |

FOREIGN PATENT DOCUMENTS

| | | |
|---|---|---|
| CN | 103673888 A | 3/2014 |
| CN | 104279953 A | 1/2015 |
| CN | 104995480 A | 10/2015 |
| JP | 2000-512401 A | 9/2000 |
| JP | 2009-122105 A | 6/2009 |
| JP | 2010-261960 A | 11/2010 |
| JP | 2012-208102 | 10/2012 |
| JP | 2013-174593 A | 9/2013 |
| JP | 2014-115242 A | 6/2014 |
| JP | 2015-014604 | 1/2015 |

OTHER PUBLICATIONS

Office Action received in Japanese Patent Application No. 2016-060274, dated Oct. 2, 2018.
Decision to Grant Patent received in Japanese Patent Application No. 2016-060274, dated Feb. 5, 2019.
Office Action in Chinese Patent Application No. CN 201710034921.3, dated Dec. 11, 2018.

| Monitored wavelength | Threshold |
|---|---|
| $\lambda_1$ | Th1 |
| $\lambda_2$ | Th2 |
| ... | ... |
| $\lambda_n$ | Thn |

FIG. 10

OPTICAL MEASUREMENT DEVICE

FIELD

The present description relates to a measurement device capable of measuring, for example, the surface topography of a measurement object using white light confocal measurement principles.

BACKGROUND

White light confocal optical measurement devices are known as devices used for examining the surface topography of a measurement object. This kind of optical measurement device includes a light source generating illumination light including a plurality of wavelength components, an optical system configured to introduce an axial chromatic aberration into the illumination light from the light source, a light receiving unit configured to separate the reflection light received from an optical system into wavelength components and to receive the light having the wavelength components, and a light guide optically connecting the light source, the optical system, and the light receiving unit. For instance, Japanese Patent Application Publication No. 2012-208102 discloses a confocal measurement device that uses confocal optics for contactless measurement of the displacement of a measurement object.

Technical Problem

For displacement sensors that use white light confocal principles, changes such as increases in returning light, tend to affect measurement. At present, it is not possible to detect these kinds of changes in the received light waveform, and the user is not aware that the received light waveform is abnormal. The user may continue to use the sensor, unaware of the increase in returning light, and unaware that the increase is reducing the measurement accuracy of the sensor. Embodiments of the present invention provide a white light confocal optical measurement device capable of detecting abnormalities in a received light waveform.

SUMMARY

An optical measurement device according to one aspect of the invention includes a light source configured to emit illumination light including a plurality of wavelength components, an optical system configured to introduce an axial chromatic aberration into the illumination light from the light source and to receive reflection light reflecting from a measurement object where at least a portion of the measurement object lies along a line extending from the optical axis of the optical system; a light receiving unit configured to separate the reflection light received at the optical system into wavelength components and thereby receive the light having the wavelength components; and a processor configured to compute the distance from the optical system to the measurement object on the basis of a received light intensity of the wavelength components received in the light receiving unit. The processor compares a received light intensity of a wavelength component to a reference value for the wavelength component for a plurality of wavelength components in a waveform representing the light received, and detects an abnormality in the received light waveform when the amount of change in the received light intensity compared to the reference value therefor is greater than or equal to a predetermined threshold for any wavelength component in the plurality of wavelength components.

The above-mentioned configuration provides a white light confocal optical measurement device capable of detecting abnormalities in a received light waveform. Note that "the distance from the optical system to the measurement object" is the distance from the optical system to a measurement position on the measurement object, and is not necessarily the shortest distance from the optical system to the measurement object. The "measurement position" is the position on the measurement object irradiated by the illumination light from the light source. The measurement position is not limited to being one position on the measurement object.

The processor may measure the displacement of the measurement object on the basis of a peak wavelength in the received light waveform when the amount of change in the received light intensity is less than the threshold for at least one of the plurality of wavelength components.

The above-mentioned configuration is capable of detecting an abnormal waveform on the basis of the received light intensity in another wavelength even if one of the wavelengths selected from among the plurality of wavelengths coincides with the measurement wavelength.

The plurality of wavelength components may include five wavelengths. The above-mentioned configuration is capable of detecting an abnormal waveform on the basis of the received light intensity within a single wavelength even when four of the wavelengths selected from among the five wavelengths coincides with the measurement wavelengths and the object to be measured is configured from two transparent bodies (such as glass) with a spacer therebetween.

The threshold may be defined for each wavelength on the basis of the spectrum emitted by the light source. The above-mentioned configuration is capable of more precise detection of an abnormal waveform by establishing a threshold for each wavelength.

An optical measurement device according to another aspect of the invention includes a light source configured to emit illumination light including a plurality of wavelength components; an optical system configured to introduce an axial chromatic aberration into the illumination light from the light source and to receive reflection light reflecting from a measurement object where at least a portion of the measurement object lies along a line extending from the optical axis of the optical system; a light receiving unit configured to separate the reflection light received at the optical system into wavelength components and thereby receive the light having the wavelength components; and a processor configured to compute the distance from the optical system to the measurement object on the basis of a received light intensity of the wavelength components received in the light receiving unit. The processor compares a reference value for a received light intensity and the received light intensity of a wavelength component outside a wavelength domain equivalent to a measurement range used to measure the displacement of the measurement object, and detects an abnormality in the received light waveform representing the received light intensity when the amount of change in the received light intensity compared to the reference value therefor is greater than or equal to a predetermined threshold.

The above-mentioned configuration is capable of monitoring the received light waveform while reducing the effects to measuring the displacement of the object.

The optical measurement device according to any of the above-mentioned aspects of the invention may be configured so that the processor provides a notification when an abnormality is detected.

The above-mentioned configuration makes the user aware that the received light waveform from the optical measurement device is abnormal. Hereby, the user may take the appropriate steps to remove the cause of the abnormality. Accordingly, this allows the optical measurement device to continue to perform highly accurate displacement measurements.

Effects

Embodiments of the present invention can detect abnormalities in a received light waveform in a white light confocal optical measurement device.

BRIEF DESCRIPTION OF THE DRAWINGS

FIG. 10 illustrates an example of the relationship between a monitored wavelength and a threshold;

DETAILED DESCRIPTION

Figure 1:
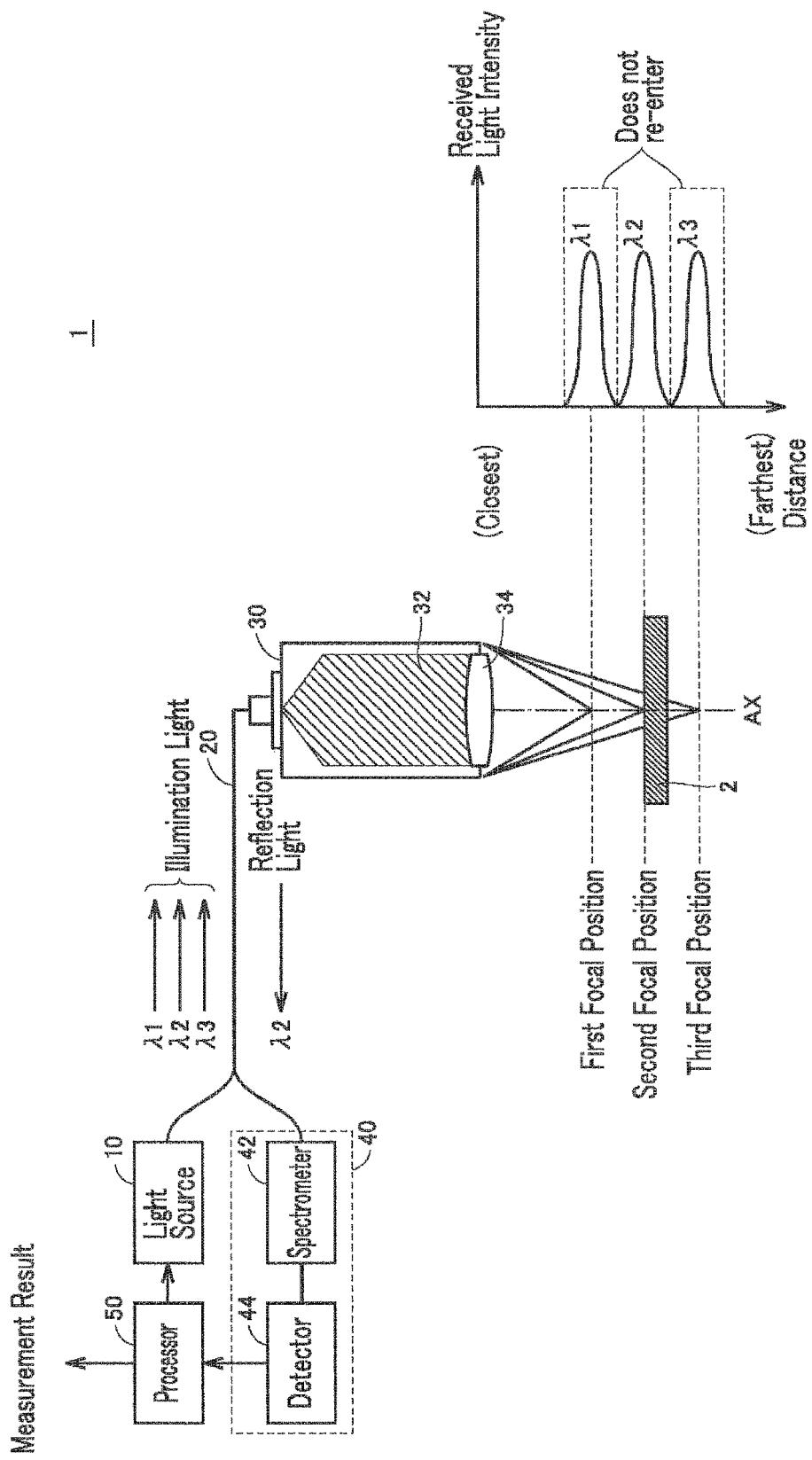
FIG. 1 is a diagram for explaining the principles of measuring displacement through white light confocal measurement.

Embodiments of the present invention are described in detail with reference to the drawings. The same or corresponding elements within the drawings are given the same reference numerals and the explanations therefor are not repeated.

A. Further Background and Overall Configuration

First, the problems to be addressed by an optical measurement device according to embodiments of the invention and an overview of a configuration for solving these problems are described.

FIG. 1 is a diagram for explaining the principles of measuring displacement through white light confocal measurement. Referring to FIG. 1, the optical measurement device 1 includes a light source 10, a light guide 20, a sensor head 30, a light receiving unit 40, and a processor 50. The sensor head 30 contains a chromatic aberration unit 32 and an objective 34; the light receiving unit 40 includes a spectrometer 42 and a detector 44.

The illumination light, which contains various specific wavelengths generated by the light source 10, propagates through the light guide 20 and arrives at the sensor head 30. The light radiating from the light source 10 is focused by the objective 34 in the sensor head 30 and illuminates the measurement object 2. As the illumination light passes through the chromatic aberration unit 32, the chromatic aberration unit 32 generates an axial chromatic aberration therein; therefore, the illumination light emerging from the objective 34 has focal points that differ by wavelength. Only light of a wavelength whose focal point coincides with the object 2 re-enters the confocal optical fiber in the light guide 20 of the sensor head 30. For the sake of brevity, the expression "reflecting only a specific optical wavelength" refers to the reflection of light with a wavelength whose focal point coincides with the position of the object 2.

The reflection light re-entering the sensor head 30 propagates through the light guide 20 and enters the light receiving unit 40. In the light receiving unit 40, the spectrometer 42 separates the reflection light entering therein into different wavelength components, and the detector 44 detects the (radiant) intensity of each of the wavelength components. The processor 50 then calculates the distance (displacement) from the sensor head 2 to the object 44 on the basis of the detection results from the detector 30.

In the example illustrated in FIG. 1, for instance, illumination light containing a plurality of wavelengths $\lambda 1, \lambda 2, \lambda 3$ is separated by wavelength, with an image being formed at different positions (e.g., the first focal point 1, second focal point 2, and third focal point 3) along an optical axis AX. The surface of the object 2 coincides with the second focal point 2 on the optical axis AX and so only the component wavelength $\lambda 2$ in the illumination light is reflected. The component wavelength $\lambda 2$ is detected in the light receiving unit 40, and the distance from the sensor head 30 to the object 2 computed as equivalent to the focal position of the wavelength $\lambda 2$.

The detector 44 in the light receiving unit 40 is made up of a plurality of light receiving elements, on receiving the reflection light a light receiving element changes relative to the sensor head in accordance with the shape of the surface of the object 2; consequently, the detection results (pixel information) from the plurality of light receiving elements in the detector 44 can be used to measure the changes in distance to (displacement of) the object 2. The optical measurement device 1 thereby measures the surface topography of the measurement object 2. Note that the distance from the sensor head 30 to the measurement object 2 is in distance from the sensor head 30 to a measurement object position on the measurement object 2, and is not limited to the shortest distance from the sensor head 30 to the measurement object 2. The measurement object position is a position on the measurement object 2 irradiated by illumination light from the light source 10. The measurement position is not limited to being one position on the measurement object. For instance, two different measurement object positions may be selected from along the direction of the optical axis of the sensor head 30. The distance is calculated from the sensor head 30 to each of the measurement object positions; the difference between the two distances is also computed. Hereby, the thickness of the measurement object 2 can be computed.

Figure 2A:
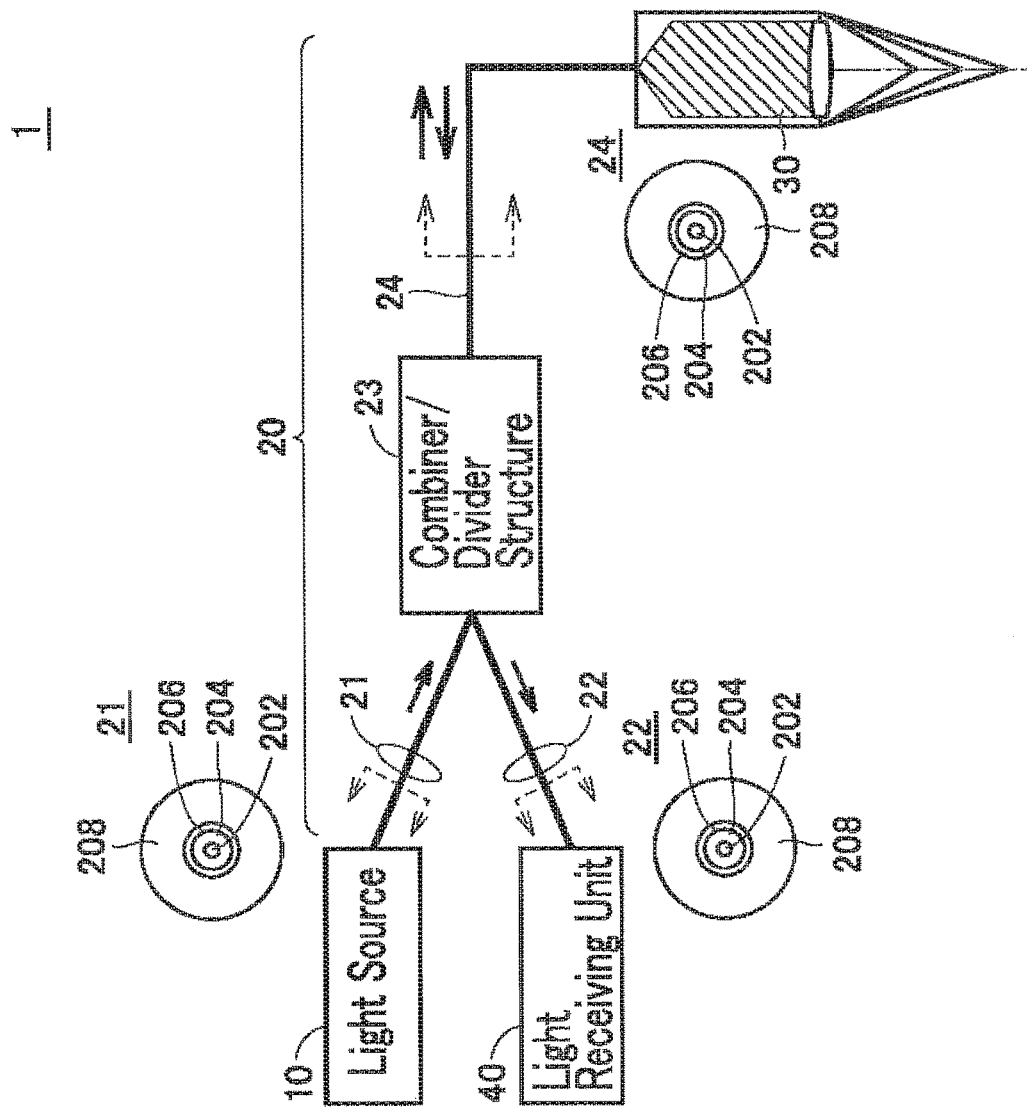
FIGS. 2A and 2B are schematic views for describing the configuration of the light guide in an optical measurement device according to the embodiments.
Figure 2B:
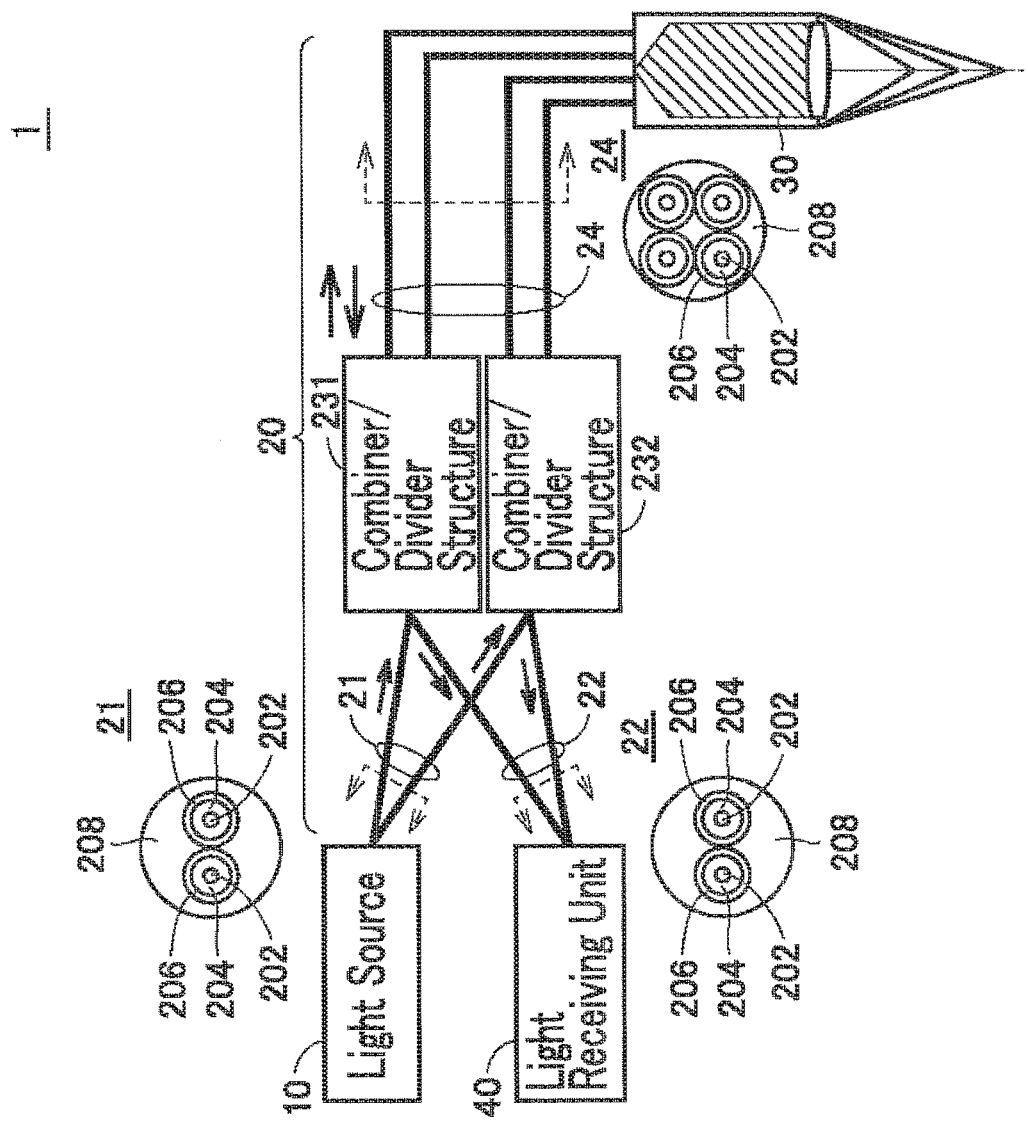

FIGS. 2A and 2B are schematic views for describing the configuration of the light guide in an optical measurement device according to the embodiments. As illustrated in FIG. 2A, the optical measurement device 1 includes an input cable 21 optically coupled to the light source 10, an output cable 22 optically coupled to the light receiving unit 40, and a sensor head cable 24 optically coupled to the sensor head 30; the input cable 21, output cable 22, and sensor head cable 24 serve as the light guide 20. The ends of the input cable 21 and the output cable 22 are optically coupled through a combiner/divider type coupler 23. The coupler 23 is 2×1 star coupler (with two inputs to one output or one input to two outputs) which is equivalent to a Y-splitter; in addition to transmitting the light entering from the input cable 21 to the sensor head cable 24, the coupler 23 splits the light entering from the sensor head cable 24 and transmits the light to the input cable 21 and the output cable 22.

The input cable 21, output cable 22, and sensor head cable 24 are all optical fibers containing a single core 202; in cross section, the core 202 is sheathed in a cladding 204, a coating 206, and an exterior jacket 208 in that order outwards. As illustrated in FIG. 2B, the optical fibers in the light guide 20 of the optical measurement device 1 according to the embodiment includes a plurality of cores.

B. Device Structure

Figure 3:
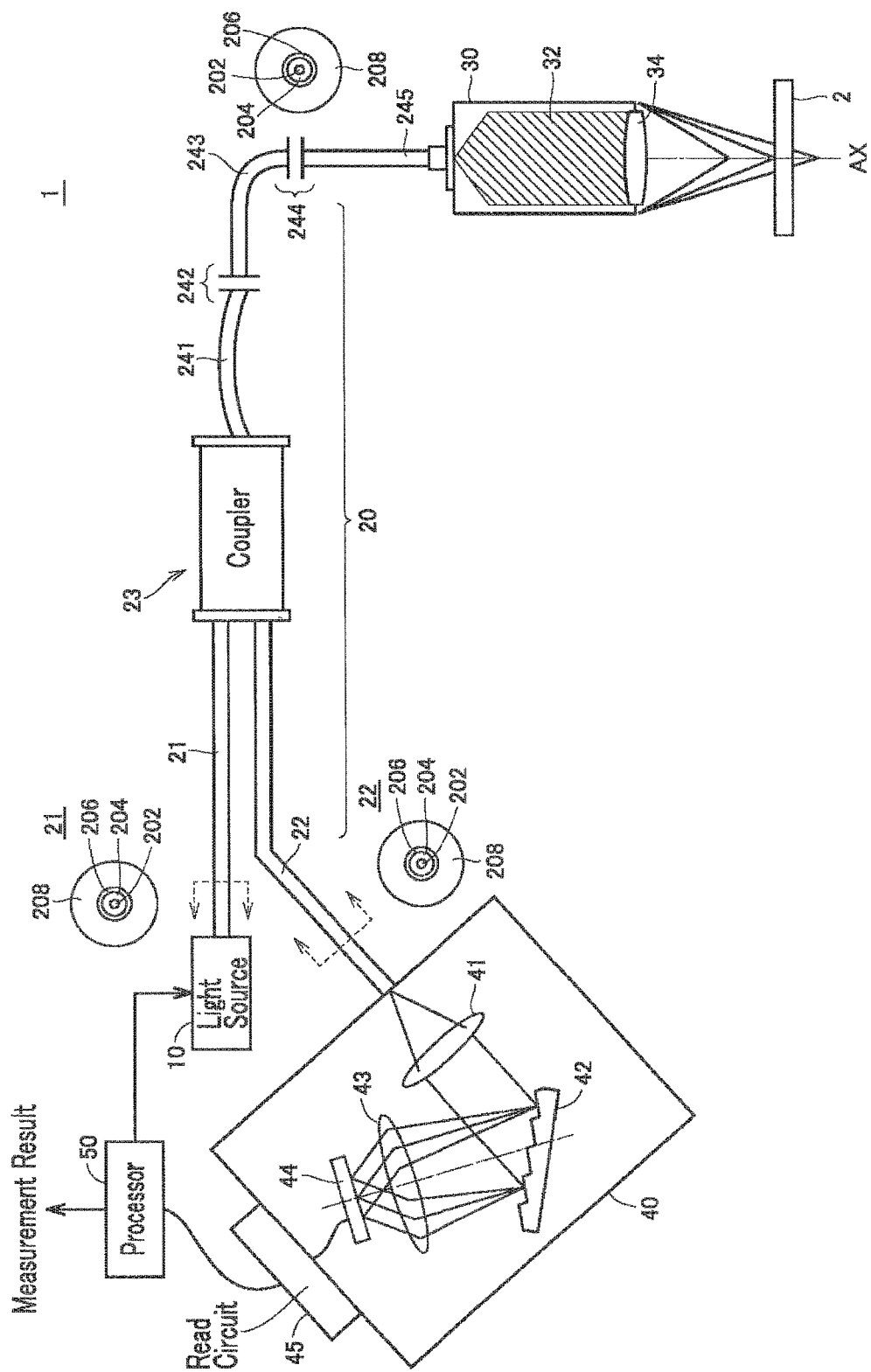
FIG. 3 is a schematic view depicting an example device configuration of an optical measurement device according to an embodiment.

FIG. 3 is a schematic view an example device configuration an optical measurement device according to an embodiment. Referring to FIG. 3, the optical measurement device 1 according to the embodiment includes a light source 10, a light guide 20, a sensor head 30, a light receiving unit 40, and a processor 50.

The light source 10 emits illumination light containing a plurality of optical wavelength components, and is typically implemented using a white-light light emitting diode (LED). Any desired kind of light source may be used, so long as the light source is capable of radiating light possessing a range of wavelengths where the displacement width of all the focal positions generated through the axial chromatic aberration covers the required measurement range.

The sensor head 30 contains a chromatic aberration unit 32 and the objective 34; the sensor head 30 is equivalent to an optical system that induces an axial chromatic aberration in light radiating from the light source 10 and receives light reflecting from the measurement object 2 with at least a portion of the measurement object 2 arranged on a line extending from the optical axis.

The light receiving unit 40 includes a spectrometer 42, and a detector 44, the spectrometer 42 separates the light reflecting from the object and received at the optical system, i.e., the sensor head 30 into each wavelength component; the detector 44 includes a plurality of light receiving elements arranged corresponding to the dispersion direction from the spectrometer 42. The spectrometer 42 is typically a diffraction grating, however any desired device may be adopted therefor. The detector 44 may be a line sensor (one-dimensional sensor) with a plurality of light receiving elements arranged one-dimensionally to correspond with the dispersion direction from the spectrometer 42. The detector 44 may also be an image sensor (two-dimensional sensor) where the light receiving elements are arranged two dimensionally on the detection surface.

In addition to the spectrometer 42 and the detector 44, the light receiving unit 40 includes a collimating lens 41 that collimates the reflection light emitted from the output cable 22, and a read circuit 45 for outputting the results from the detector 44 to the processor 50. Furthermore, reduction optics 43 may also be provided as needed, to modify the spot size of the reflection light separated into wavelengths by the spectrometer 42.

The processor 50 computes the distance between the sensor head 30 and the measurement object 2 on the basis of the detection values from each light receiving element among the plurality of light receiving elements in the light receiving unit 40. A relational expression between a pixel, a wavelength, and a distance value can be preliminarily set, for instance, by being permanently stored in the processor 50 when shipping the device. Therefore, the processor 50 can compute the displacement using the received light waveform (i.e., pixel information) output from the light receiving unit 40.

FIG. 3 illustrates an example of a sensor head cable with a plurality of cables connected in series, this arrangement is for improving usability. That is, the sensor head cable in this example contains three cables 241, 243, 245. A connector 242 is inserted between the cable 241 and the cable 243 to optically connect the cables, and another connector 244 is inserted between the cable 243 and the cable 245 to optically connect the cables.

The light guide 20 contains a combiner/divider (coupler) 23 for optically coupling the input cable 21 and output cable 22 with the sensor head cable. The functions of the combiner/divider 23 were already described with reference to FIG. 2, and thus a description therefor is not repeated here.

With a combiner/divider serving as the coupler in the optical measurement device 1 according to the embodiment, it is thereby possible to split the light within the light guide 20, and allow a single detector 44 to receive the light reflecting from the measurement object 2 (measurement light) and propagating through the plurality of cores.

C. Problems with the Reflection Light

In principle, only the wavelength component in focus at the position of the surface of the measurement object 2 is reflected therefrom and enters the light receiving unit 40. Despite that, a portion of the illumination light may reflect partway through the light receiving unit 40 (i e, along the optical path of the illumination light from the light source 10 to the sensor head); that reflection light may then enter the light receiving unit 40.

Figure 4:
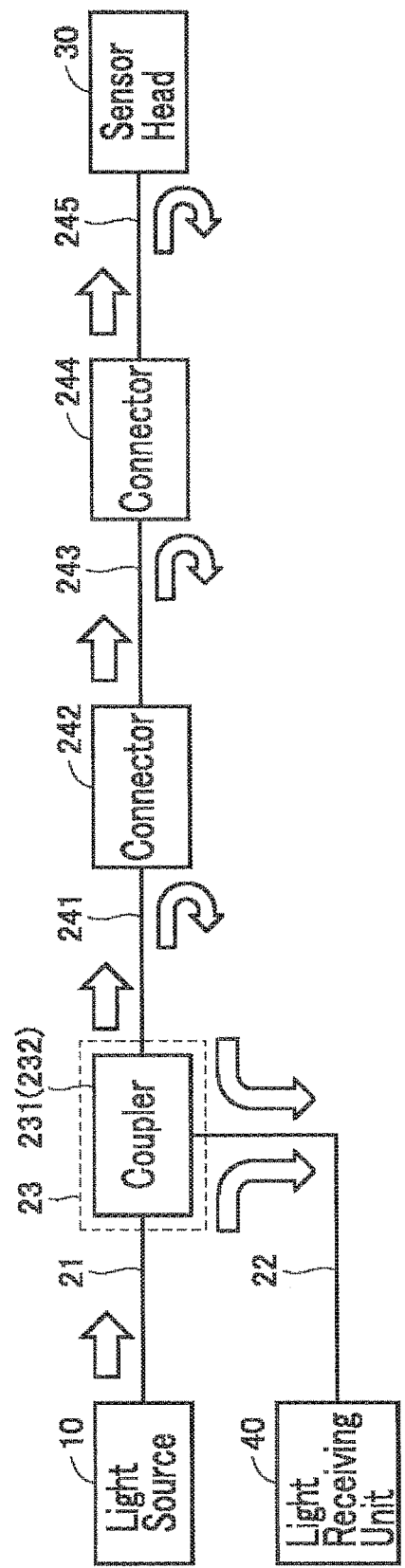
FIG. 4 is a schematic view for explaining the reflection of a portion of the illumination light partway through the light guide.

FIG. 4 is a schematic view for explaining the reflection of a portion of the illumination light partway through the light guide 20. As illustrated in FIG. 4, this reflection of a portion of illumination light may occur, for instance in the combiner/divider 23 (coupler 231, 232), connector 242, connector 244, or the connecting part between the sensor head 30 and the cable 245. Increasing or decreasing the power of the light source 10 can also bring about abnormalities in the returning light.

A portion of the illumination light may reflect and return to the sensor head when, for instance, the combiner/divider 23 is defective, or the connector 242, 244 is damaged or dirty. The illumination light is possibly scattered inside the optical fiber when a longer optical fiber is included in the cable. Moreover, a portion of the illumination light may be reflected by damage or dirt on the end surface of the fiber.

Figure 5:
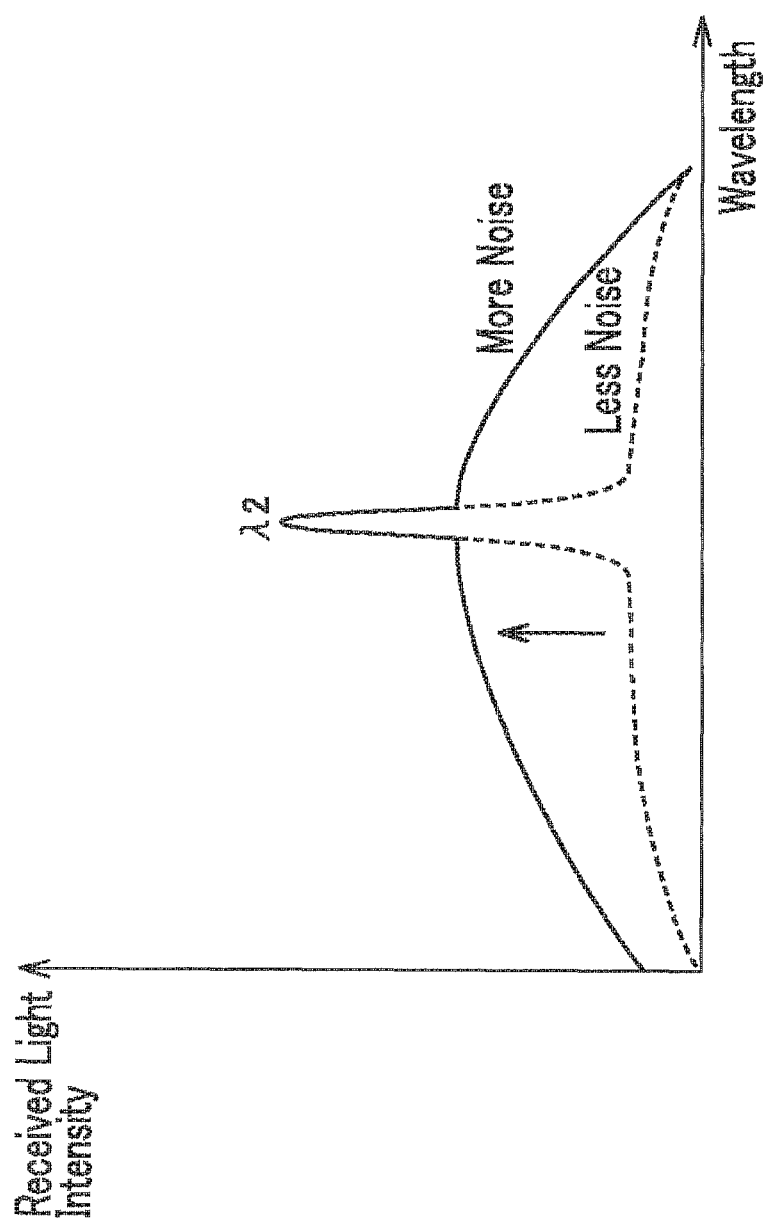
FIG. 5 is a schematic view for explaining the problems that arise when a portion of the illumination light is reflected partway through the light guide.

FIG. 5 is a schematic view for explaining the problems that arise when a portion of the illumination light is reflected partway through the light guide 20. Referring to FIG. 5, the processor 50 identifies the peak position of the (radiant) intensity of the received light on the basis of the received light waveform (i.e., the radiant intensity profile of the received light). The processor 50 identifies a main component wavelength among the wavelengths included in the reflection light from the wavelength corresponding to said peak position; the processor 50 then computes the distance from the sensor head to the measurement object 2 (i.e. the displacement) on the basis of the main component wavelength identified (e.g., the wavelength $\lambda 2$).

When the optical measurement device 1 is operating normally, the amount of noise component (i.e., the background noise) detected is sufficiently small. However, when a portion of the illumination light reflects in and reenters the light guide 20, the (radiant) intensity of the received light increases in the noise components, i.e., in the wavelengths other than wavelength $\lambda 2$.

Figure 6A:
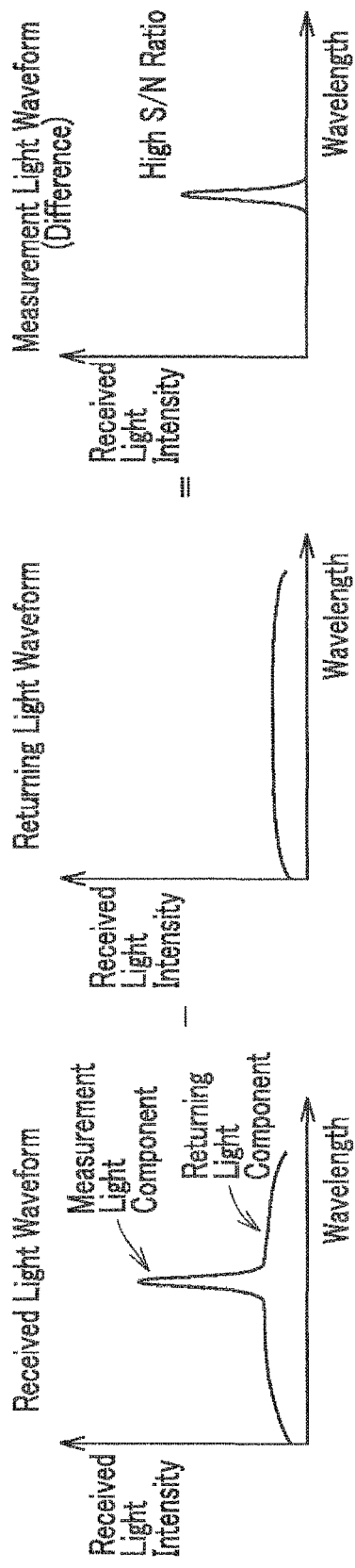
FIGS. 6A and 6B are for describing how received signals are processed within an optical measurement device according to the embodiment.
Figure 6B:
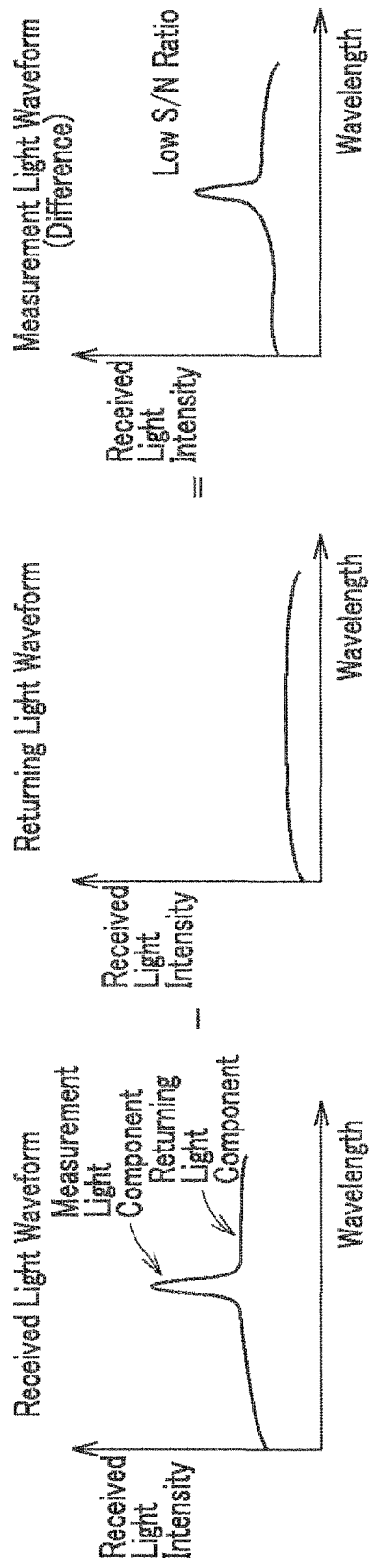

FIGS. 6A and 6B are for describing how received signals are processed within an optical measurement device 1 according to the embodiment. FIG. 6A is a waveform diagram for describing the received light waveform obtained when the optical measurement device 1 is operating normally. FIG. 6B is a waveform diagram for describing the received light waveform obtained when the optical measurement device 1 is operating abnormally.

As illustrated in FIG. 6A and in FIG. 6B, the optical measurement device 1 according to the embodiment identifies the main component wavelength on the basis of the received light waveform and a waveform generated by subtracting a returning light waveform (i.e. obtaining the measurement waveform). For instance, the returning light waveform can be obtained before measuring the displacement, and stored internally in the optical measurement device 1.

During normal operation of the optical measurement device 1, there is a small difference between the returning light component contained in the received light waveform and the returning light within the waveform acquired in advance. The measurement waveform essentially cancels out the returning light component, and thus the signal-to-noise ratio is high. Therefore, it is possible to very accurately identify the main component wavelength.

Whereas, as illustrated in FIG. 6B, when there is a large returning light component in the received light waveform, the returning light component within the received light waveform is not canceled out even if there is a difference between the received light waveform and the preliminarily stored returning light component waveform. Therefore, the signal-to-noise ratio of the measurement waveform is low. The lower signal-to-noise ratio reduces the accuracy of detecting the peak wavelength, and therefore reduces the accuracy of measuring the displacement.

In the embodiment, the processor 50 monitors the received light intensity of a specific wavelength. The processor 50 detects a received light waveform as abnormal when the change between the received light intensity in the specific wavelength is greater than or equal to a threshold in relation to the received light intensity when the optical measurement device is operating normally. Moreover, the processor 50 provides notification of the abnormality. The user may then, for instance, clean the connectors 242, 244 or exchange the light guide 20 to thereby remove the cause of the abnormal waveform. Additionally, if the amount of returning light increases because of lengthening the optical fiber for instance, the value of the returning light component may be re-acquired and stored internally in the optical measurement device 1 to thereby remove the cause of the abnormal waveform. Accordingly, this allows the optical measurement device to continue to perform highly accurate displacement measurements. Embodiments of the invention are described below in detail.

D. First Embodiment

Figure 7:
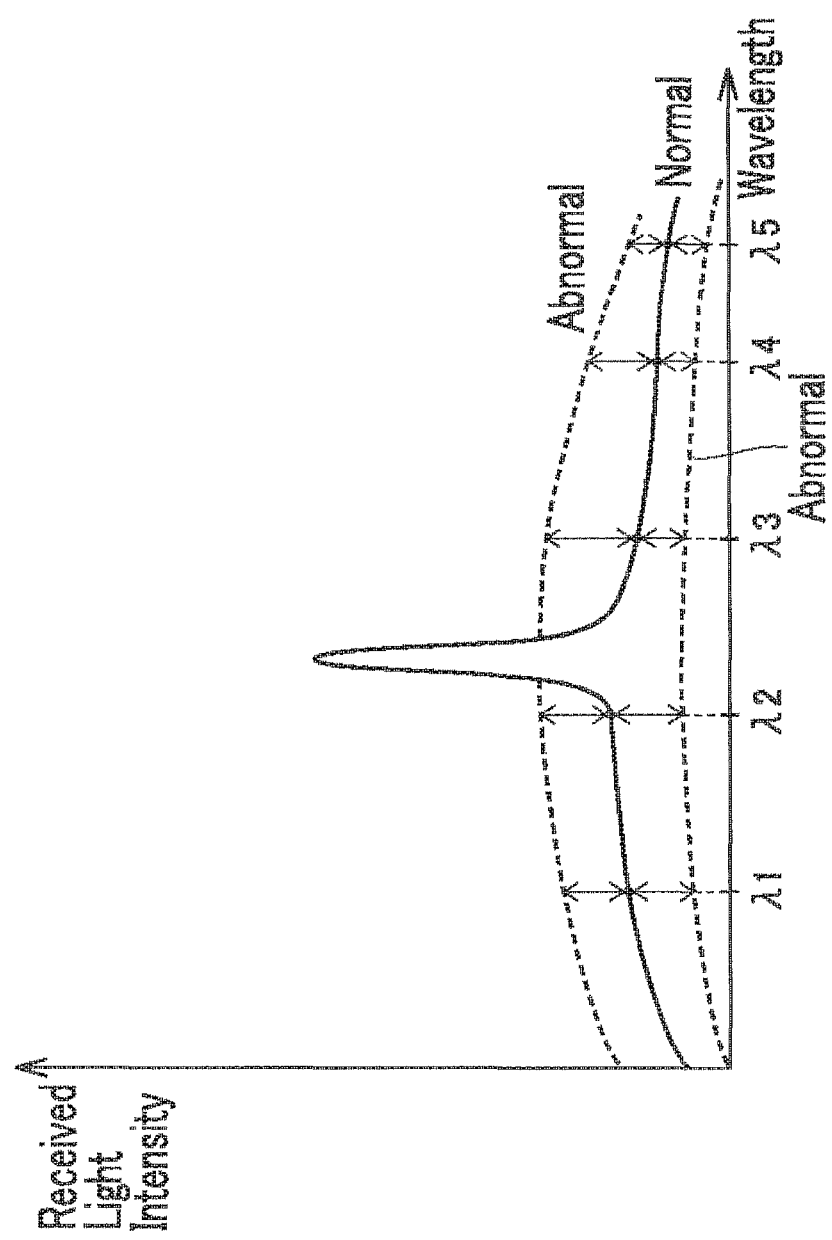
FIG. 7 is a schematic waveform diagram for explaining how the optical measurement device assesses abnormalities according to the first embodiment.

FIG. 7 is a schematic waveform diagram for explaining how, according to the first embodiment, the optical measurement device 1 assesses abnormalities. Referring to FIG. 3 and FIG. 7, the light receiving unit 40 measures the received light intensity 11, 12, 13, 14, 15 in the wavelengths $\lambda 1, \lambda 2, \lambda 3, \lambda 4, \lambda 5$ respectively. The processor 50 compares the received light intensity in each of the wavelengths with a reference value for the wavelength (i.e., the received light intensity during normal operation). For instance, the reference value may be set initially when shipping the product. When swapping a sensor head in or out on site, the user may press an operation button (not shown) on the optical measurement device 1 to reset the reference values.

The processor 50 determines, for each of the wavelengths whether or not the difference between the received light intensity and the reference value exceeds a threshold. If the difference between the received light intensity and the reference value exceeds the threshold for all the wavelengths $\lambda 1, \lambda 2, \lambda 3, \lambda 4, \lambda 5$, the processor 50 determines there is an abnormality in the optical measurement device 1. The reference value and the threshold may be set for each wavelength and stored internally in the processor 50.

More wavelengths may be used for comparing the received light intensity and the reference value than the number of surfaces on the measurement object 2 for which the displacement is measured. The optical measurement device 1 may detect a plurality of surfaces; this may occurs when the measurement object 2 is transparent. When the measurement object 2 is transparent, the peaks appear in received light waveform, the number of peaks corresponds to the number of wavelengths, which corresponds to the number of front surfaces and rear surfaces on the transparent measurement object 2. The number of thresholds is determined in accordance with the peaks in the received light waveform. Displacement is measured is for at least one surface. Hereby it is possible to detect an abnormal waveform on the basis of the received light intensity in another wavelength even if one of the wavelengths selected from the plurality of wavelengths coincides with the measurement wavelength.

Figure 8:
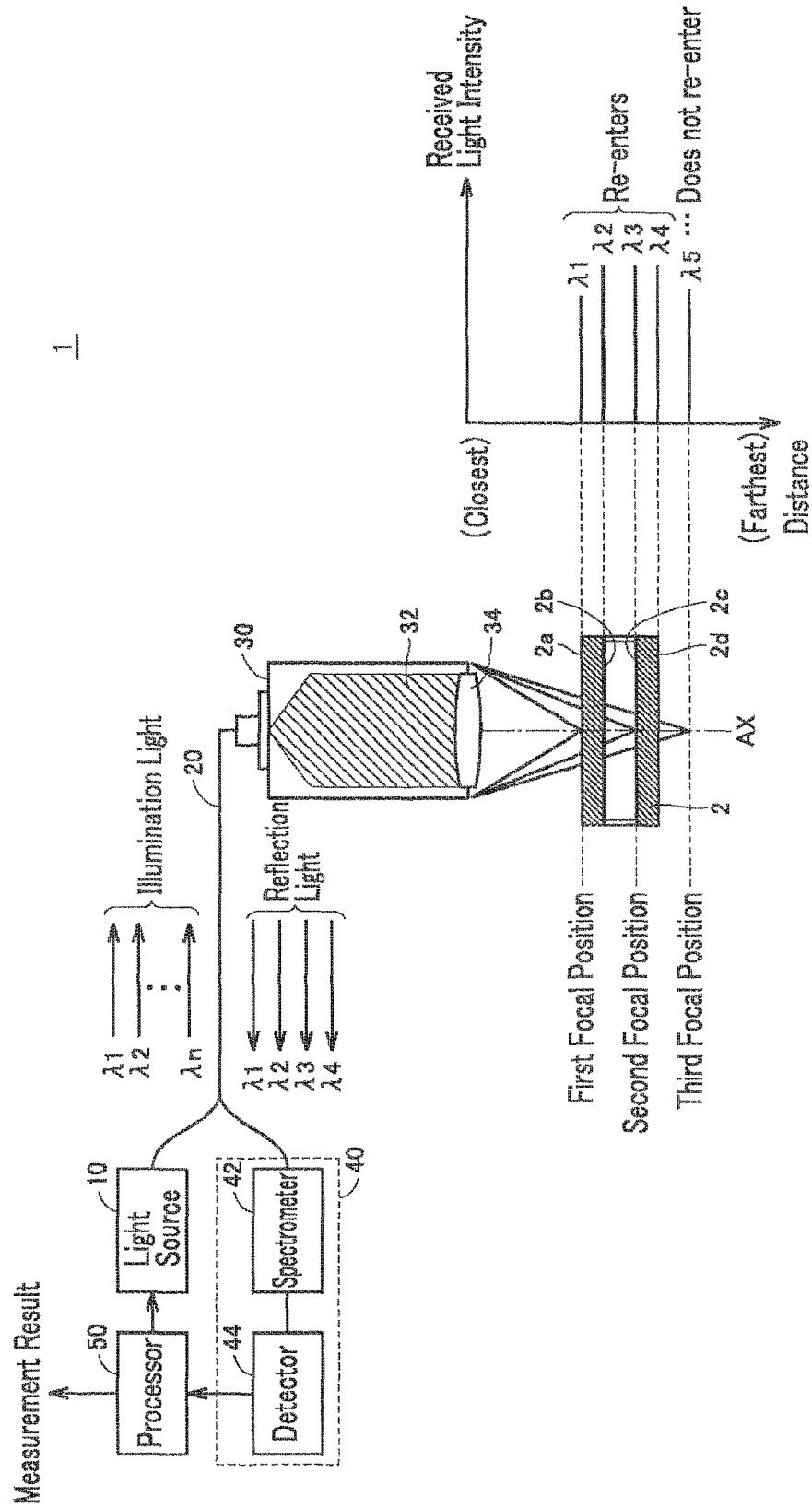
FIG. 8 is a diagram for explaining how the optical measurement device according to the embodiment measures the displacements of a plurality of surfaces on the measurement object.

Next, the reason for using five wavelengths in the first embodiment is given below. FIG. 8 is a diagram for explaining how the optical measurement device 1 according to the embodiment measures the displacements of a plurality of surfaces on the measurement object 2.

As illustrated in FIG. 8, the measurement object 2 is, for instance, made up of two transparent bodies (e.g. glass) with a spacer interposed to create a space therebetween. The measurement object 2 contains four surfaces 2A, 2b, 2c, 2d with different displacements; these four surfaces are the two front surfaces (*2a*, *2b*) of the transparent bodies and the two rear surfaces (*2c*, *2d*) of the transparent bodies. Therefore, the optical measurement device 1 measures the displacements of the two front surfaces and the two rear surfaces of the transparent bodies. The wavelength used to detect an abnormal waveform may be selected as desired. However, although all four wavelengths may be selected to detect the abnormal waveform, it is necessary to consider the possibility that the four wavelengths selected will coincide with a wavelength whose focal point is at the two front surfaces or the two rear surfaces of the measurement object 2 (i.e., the two transparent bodies). It is therefore necessary to ensure the number of wavelengths differs from the number of surfaces to be detected.

In the example illustrated in FIG. 8, the focal position for the wavelength component λ5 in the illumination light differs from the positions of the surfaces *2a*, *2b*, *2c*, *2d*. Therefore, the optical measurement device 1 can detect an abnormality by comparing the wavelength component λ5 in the received light waveform and the reference value.

A user may use machine learning results to set the wavelengths and thresholds. The wavelengths and thresholds may be established in accordance with the spectrum emitted by the light source 10. Note that the wavelengths and thresholds may be set in advance, for instance, when shipping the optical measurement device.

Figure 9:
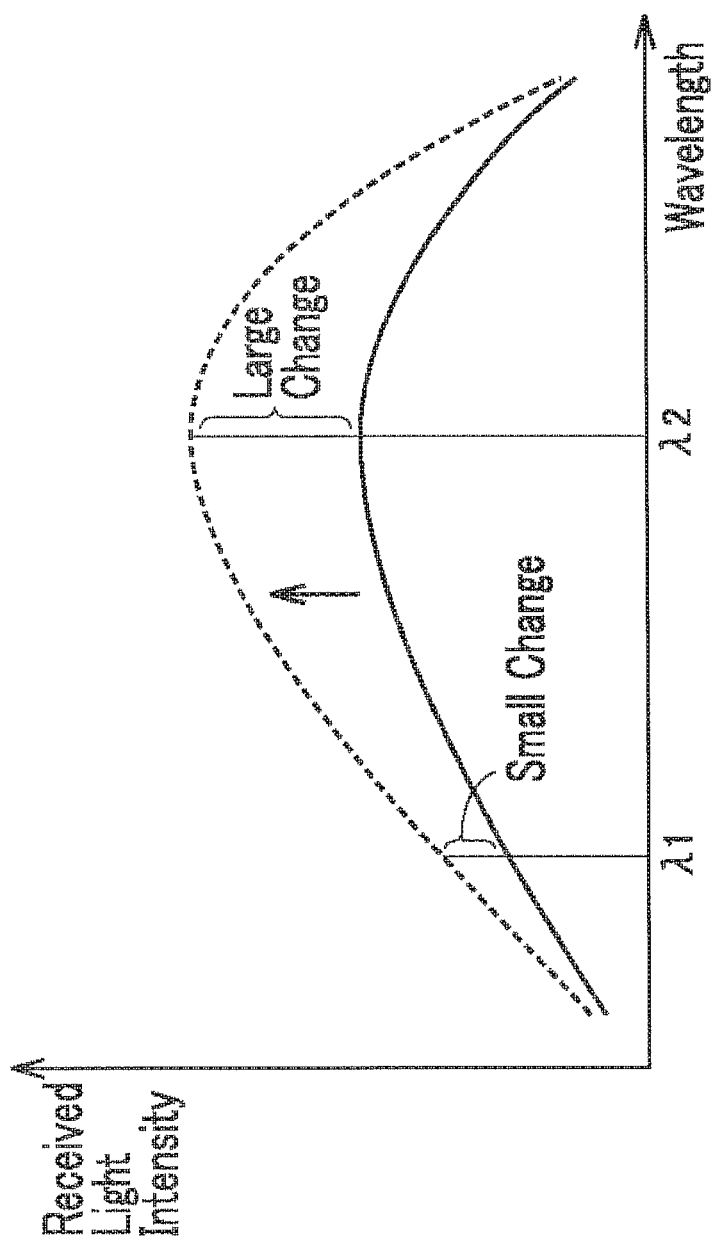
FIG. 9 schematically illustrates changes in the received light intensity of background components when a portion of the illumination light reflects partway through the light guide.

FIG. 9 schematically illustrates changes in the received light intensity of background components when a portion of the illumination light reflects partway through the light guide 20. Referring to FIG. 9, when a portion of the illumination light is reflected partway in the light guide 20, the amount of change in the returning light components depends on the wavelength. For instance, the threshold for a wavelength close to the peak of the returning light component is relatively greater than other thresholds because the amount of change in the returning light component tends to be larger. In contrast, for wavelengths shorter or longer than the peak wavelength in the returning light component, the threshold is relatively smaller than the other thresholds because the amount of change in the returning light component tends to be smaller. It is hereby possible to perform more precise detection of an abnormal wave form.

FIG. 10 illustrates an example of the relationship between a monitored wavelength and a threshold. As depicted in FIG. 10, n thresholds Th1, Th2, . . . , Thn are established for n wavelengths λ1, λ2, . . . , λn, where n is an integer greater than or equal to 2. In FIG. 8, n=5; further, the relationship depicted in FIG. 10 is stored in the processor 50.

Figure 11:
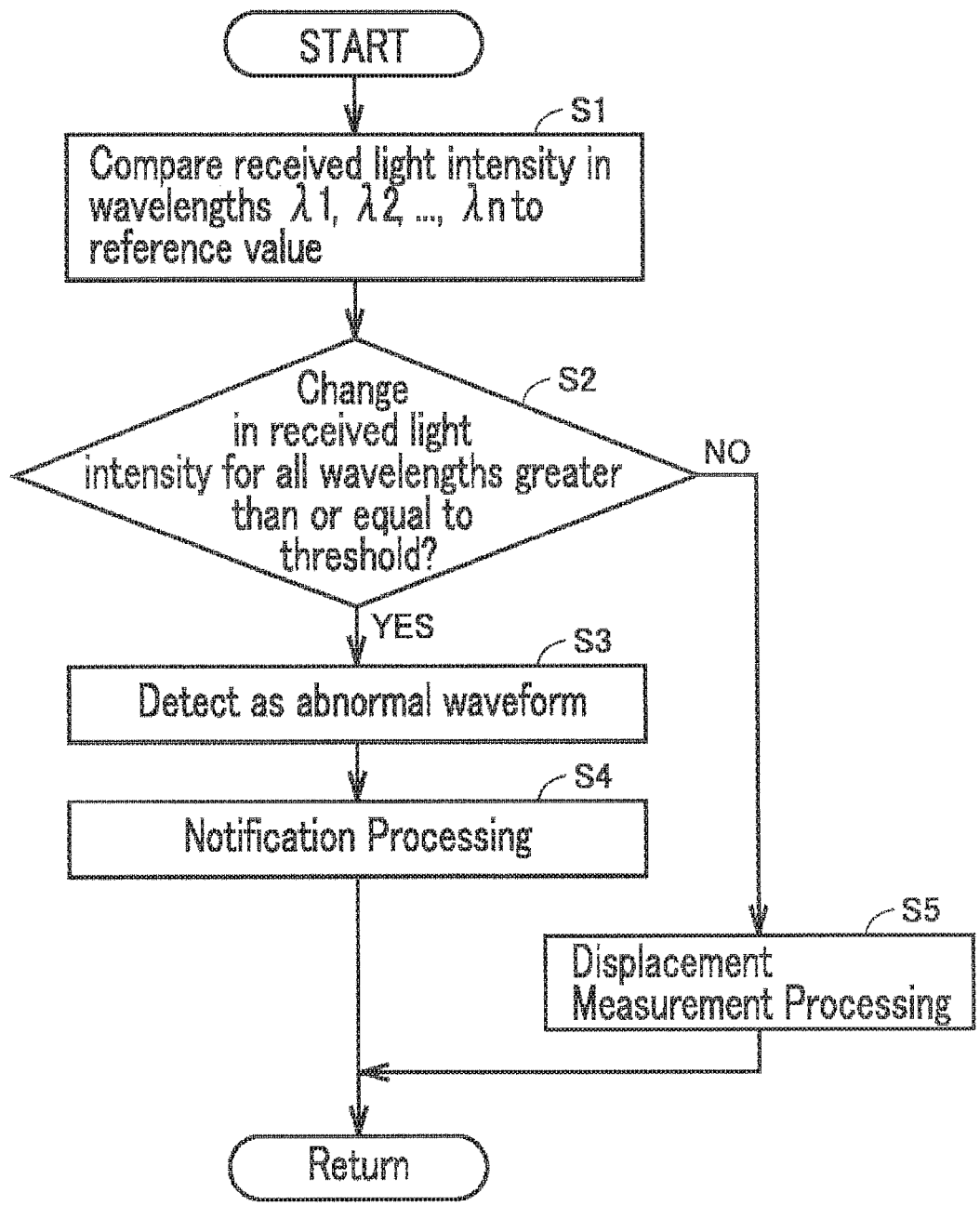
FIG. 11 is a flowchart for explaining the process of detecting an abnormal waveform according to the first embodiment.

FIG. 11 is a flowchart for explaining the process of detecting an abnormal waveform according to the first embodiment. Referring to FIG. 3 and FIG. 11, once processing starts, in step S1 the processor 50 compares the received light intensity (i.e., the wavelength component) for each of the wavelengths λ1, λ2, . . . , λn with the reference value. In step S2, the processor 50 determines whether or not the amount of change in the received light intensity is greater than or equal to the threshold for all the wavelengths.

If the amount of change in the received light intensity in relation to the reference value is greater than or equal to the threshold in all the wavelengths (YES, at step S2), in step S3, the processor 50 detects there is an abnormal waveform. In this case, in step S4 the processor 50 alerts the user that an abnormal waveform was detected. The method of notification is not particularly limited, and may be as sound or light via a known method.

Whereas, if the amount of change in the received light intensity in relation to the reference value is less than the threshold for at least one wavelength (NO, at step S2), in step S5, the processor 50 measures the displacement on the basis of the received light waveform. After the measurement of the displacement is complete, the flow returns to step S1.

E. Second Embodiment

In a second embodiment, the optical measurement device 1 detects an abnormal waveform on the basis of the amount of change in the received light intensity for a single wavelength. This optical measurement device 1 is configured identically to the first embodiment; therefore, the description of the configuration is not repeated.

Figure 12:
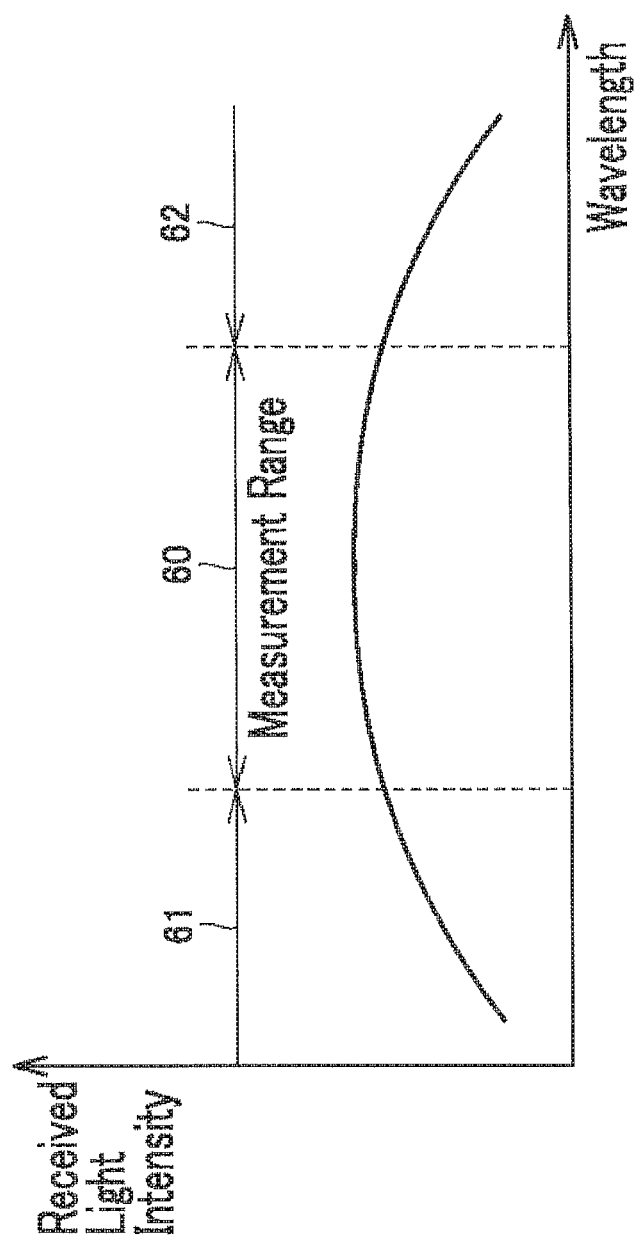
FIG. 12 is a diagram for describing the spectrum emitted by the light source to explain the process of detecting an abnormal waveform according to the second embodiment.

FIG. 12 is a diagram for describing the spectrum emitted by the light source 10 to explain the process of detecting an abnormal waveform according to the second embodiment. Referring to FIG. 12, a wavelength domain 60 is the wavelength domain used for measuring the displacement and is referred to as the "measurement range". To detect abnormal waveform in the second embodiment, a single wavelength is selected from a wavelength domain 61 or a wavelength domain 62, which are outside the measurement range. As with the first embodiment, a waveform is detected as an abnormal waveform when the amount of change in the received light intensity (wavelength component) within the selected wavelength is greater than or equal to a threshold. Consequently, the effects on measuring the displacement of the object can be reduced because the received light intensity is monitored in a single wavelength selected from a wavelength domain outside the measurement range.

Figure 13:
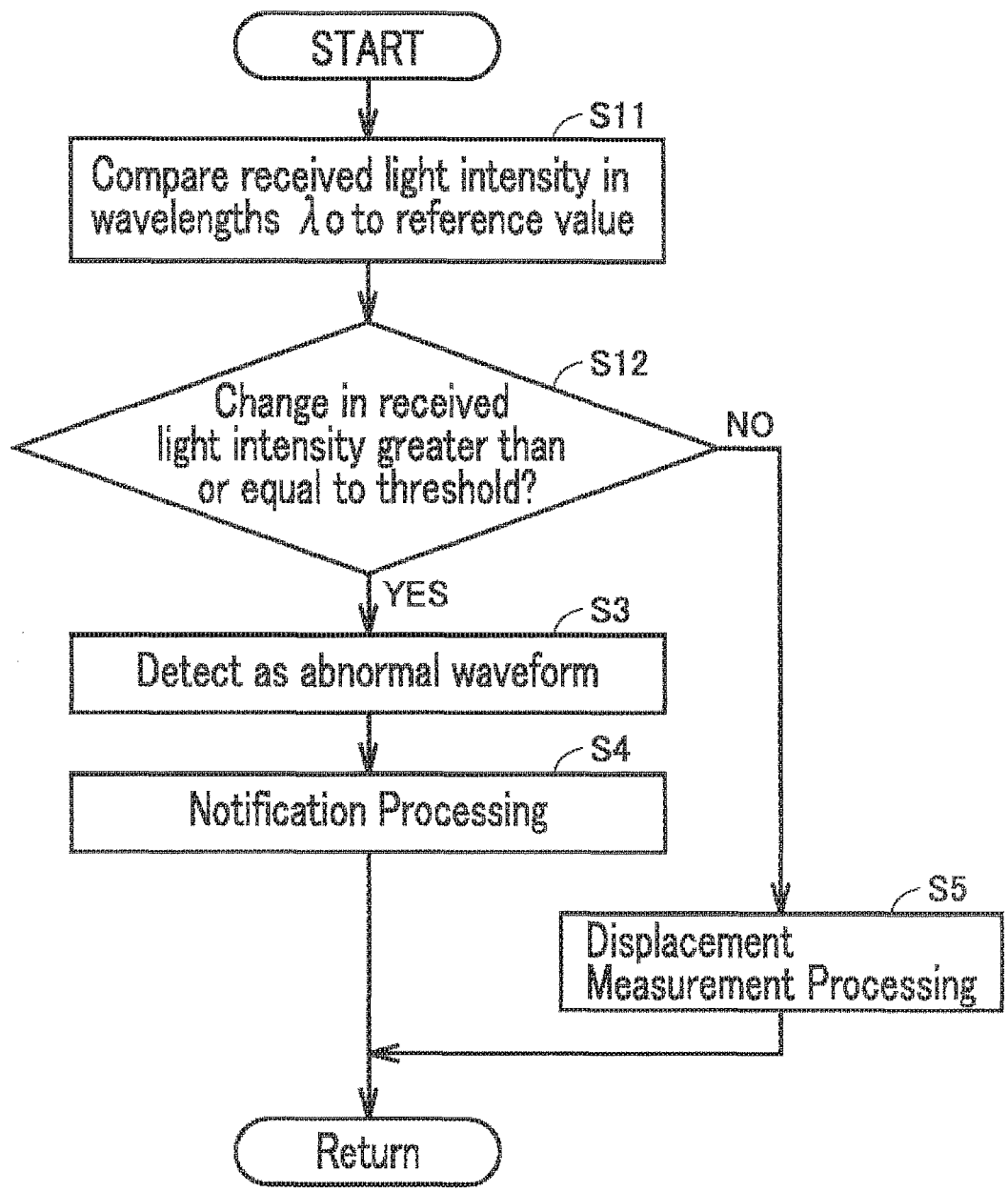
FIG. 13 is a flowchart for explaining the process of detecting an abnormal waveform according to the second embodiment.

FIG. 13 is a flowchart for explaining the process of detecting an abnormal waveform according to the second embodiment. Referring to FIG. 11 and FIG. 13, that is S11 and S12 are executed in place of steps S1 and S2 in the second embodiment. In step S11 processor 50 compares the received light intensity of a wavelength $\lambda_o$ outside the wavelength domain 60 to the reference value. The wavelength $\lambda_o$ is established in advance. In step S12, the processor 50 determines whether or not the amount of change in the received light intensity is greater than or equal to the threshold for the wavelength $\lambda_o$.

If the amount of change in the received light intensity in relation to the reference value is greater than or equal to the threshold (YES, at step S12), the processor 50 continues to step S3 and detects that there is an abnormal waveform. In step S4, the processor 50 alerts the user that an abnormal waveform was detected. In contrast, if the amount of change in the received light intensity in relation to the reference value is less than the threshold (NO, at step S12), the processor 50 continues to step S5. Here, the processor 50 measures the displacement. After measurement of the displacement is complete, the flow returns to step S11.

Note that in the second embodiment, determining whether or not the received light waveform is abnormal is carried out based on the amount of change in a wavelength outside the measurement range. Therefore, a plurality of wavelengths may be selected from within a wavelength domain outside the measurement range, and the detection of an abnormal waveform carried out on the basis of the amount of change in the received light intensity in the plurality of wavelengths.

F. Advantages

As above described, an optical measurement device 1 according to the embodiments detects whether a received light waveform is abnormal. Moreover, the optical measurement device according to the embodiments ensures a user is made aware that the received light waveform is abnormal. When an increase in the returning light reduces the measurement accuracy, the device detects the abnormality in the received light waveform. A user may take appropriate action to improve the reduced accuracy upon notification from the optical measurement device 1, e.g., cleaning a connector, and, if there is an increase in the returning light because of lengthening the optical fiber, the user may re-acquire the value for the returning light component, and store the value in the processor. Therefore, it is possible to re-establish highly accurate measurement even when the accuracy of measuring the displacement had deteriorated.

All aspects of the embodiments disclosed should be considered merely examples and not limitations as such. The scope of the present invention is not limited to the above description but to the description in the claims, and is intended to include all equivalents and modifications allowable by the claims.

What is claimed is:

1. An optical measurement device comprising:
    a light source configured to emit illumination light including a plurality of wavelength components;
    an optical system configured to introduce an axial chromatic aberration into the illumination light from the light source and to receive reflection light reflecting from a measurement object where at least a portion of the measurement object lies along a line extending from the optical axis of the optical system;
    a light receiving unit configured to separate the reflection light received at the optical system into wavelength components and thereby receive the light having the wavelength components; and
    a processor configured to compute the distance from the optical system to the measurement object on the basis of a received light intensity of the wavelength components received in the light receiving unit;
    the processor compares a received light intensity of a wavelength component to a reference value for the wavelength component for a plurality of wavelength components in a waveform representing the light received, detects an abnormality in the received light waveform when a difference between the received light intensity and the reference value therefor is greater than or equal to a predetermined threshold for all wavelength components in the plurality of wavelength components, and measures the displacement of the measurement object when the difference between the received light intensity and the reference value therefor is less than the predetermined threshold for at least one wavelength component in the plurality of wavelength components.

2. The optical measurement device according to claim 1, wherein the processor measures the displacement of the measurement object on the basis of a peak wavelength in the received light waveform when the amount of change in the received light intensity is less than the threshold for at least one of the plurality of wavelength components.

3. The optical measurement device according to claim 1, wherein the plurality of wavelength components includes five wavelengths.

4. The optical measurement device according to claim 1, wherein said threshold is defined for each wavelength on the basis of the spectrum emitted by the light source.

5. The optical measurement device according to claim 2, wherein, the processor provides notification of the abnormality when the abnormality is detected.

6. The optical measurement device according to claim 2, wherein said threshold is defined for each wavelength on the basis of the spectrum emitted by the light source.

7. The optical measurement device according to claim 6, wherein, the processor provides notification of the abnormality when the abnormality is detected.

8. The optical measurement device according to claim 2, wherein the plurality of wavelength components includes five wavelengths.

9. The optical measurement device according to claim 8, wherein, the processor provides notification of the abnormality when the abnormality is detected.

10. The optical measurement device according to claim 8, wherein said threshold is defined for each wavelength on the basis of the spectrum emitted by the light source.

11. The optical measurement device according to claim 10, wherein, the processor provides notification of the abnormality when the abnormality is detected.

12. The optical measurement device according to claim 3, wherein, the processor provides notification of the abnormality when the abnormality is detected.

13. The optical measurement device according to claim 3, wherein said threshold is defined for each wavelength on the basis of the spectrum emitted by the light source.

14. The optical measurement device according to claim 13, wherein, the processor provides notification of the abnormality when the abnormality is detected.

15. The optical measurement device according to claim 4, wherein, the processor provides notification of the abnormality when the abnormality is detected.

16. The optical measurement device according to claim 1, wherein, the processor provides notification of the abnormality when the abnormality is detected.

* * * * *